(12) United States Patent
McGregor et al.

(10) Patent No.: US 11,737,805 B2
(45) Date of Patent: Aug. 29, 2023

(54) CRYOABLATION DEVICES AND RELATED METHODS

(71) Applicant: Regents of the University of California, Oakland, CA (US)

(72) Inventors: Hugh McGregor, San Francisco, CA (US); Miles Conrad, San Francisco, CA (US); Mark Wilson, San Francisco, CA (US); Andrew Surman, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 617 days.

(21) Appl. No.: 16/645,979

(22) PCT Filed: Sep. 14, 2018

(86) PCT No.: PCT/US2018/051106
§ 371 (c)(1),
(2) Date: Mar. 10, 2020

(87) PCT Pub. No.: WO2019/055800
PCT Pub. Date: Mar. 21, 2019

(65) Prior Publication Data
US 2020/0275968 A1   Sep. 3, 2020

Related U.S. Application Data

(60) Provisional application No. 62/558,498, filed on Sep. 14, 2017.

(51) Int. Cl.
*A61B 18/14*   (2006.01)
*A61B 18/02*   (2006.01)
(Continued)

(52) U.S. Cl.
CPC ............. *A61B 18/02* (2013.01); *A61M 25/09* (2013.01); *A61B 2018/0022* (2013.01);
(Continued)

(58) Field of Classification Search
CPC ............ A61B 18/02; A61B 2018/0022; A61B 2018/00279; A61B 2018/00285;
(Continued)

(56) References Cited

U.S. PATENT DOCUMENTS 5,100,388 A * 3/1992 Behl ..................... A61B 18/082
                                                              604/113
5,951,514 A * 9/1999 Sahota ............... A61M 25/1011
                                                              604/101.05
(Continued)

FOREIGN PATENT DOCUMENTS

WO          0197702 A1      12/2001

*Primary Examiner* — Michael F Peffley
*Assistant Examiner* — Amanda L Zink
(74) *Attorney, Agent, or Firm* — Fredrikson & Byron, P.A.

(57) ABSTRACT

Disclosed herein are cryoablation devices and methods of using the same, including to ablate gallbladders. In certain implementations, the device is a catheter that has an expandable cryogen balloon for expansion within a gallbladder and at least one suction opening for applying suction within the gallbladder. According to other implementations, the device has a cryogen probe and a suction catheter slidably positioned on the probe.

20 Claims, 8 Drawing Sheets

(51) Int. Cl.
*A61M 25/09* (2006.01)
*A61B 18/00* (2006.01)

(52) U.S. Cl.
CPC ............... *A61B 2018/00482* (2013.01); *A61B 2018/00577* (2013.01); *A61B 2018/0212* (2013.01); *A61B 2218/007* (2013.01)

(58) Field of Classification Search
CPC ........... A61B 2018/00291; A61B 2018/00482; A61B 2018/00577; A61B 2018/0212; A61B 2218/007
See application file for complete search history.

(56) References Cited

U.S. PATENT DOCUMENTS

| | | | |
|---|---|---|---|
| 6,270,493 B1* | 8/2001 | Lalonde | A61B 18/02 606/23 |
| 6,623,516 B2* | 9/2003 | Saab | A61F 7/123 607/113 |
| 7,101,367 B2* | 9/2006 | Xiao | A61B 18/02 606/23 |
| 9,474,881 B2 | 10/2016 | Razavi | |
| 2005/0113743 A1 | 5/2005 | Ad | |
| 2005/0240147 A1 | 10/2005 | Makower et al. | |
| 2007/0293724 A1* | 12/2007 | Saadat | A61B 1/015 600/156 |
| 2009/0143760 A1* | 6/2009 | Van Dam | A61B 17/11 606/174 |
| 2020/0360670 A1* | 11/2020 | Legum | A61M 25/10 |

\* cited by examiner

CRYOABLATION DEVICES AND RELATED METHODS

CROSS-REFERENCE TO RELATED APPLICATION(S)

This application claims priority to International PCT Application No. PCT/US18/51106, filed on Sep. 14, 2018, which claims the benefit under 35 U.S.C. § 119(e) to U.S. Provisional Application 62/558,498, filed Sep. 14, 2017 and entitled "Cryoablation Catheter and Related Methods," which is hereby incorporated herein by reference in its entirety.

FIELD OF THE INVENTION

The various embodiments herein relate to methods and ablation devices for treating gallbladder disease.

BACKGROUND OF THE INVENTION

Gallstone disease affects 20 million people annually in the United States and results in more than 200,000 surgical cholecystectomies being performed each year.

The standard of care for acute cholecystitis is the laparoscopic cholecystectomy.

Unfortunately, the complication rate in the elderly undergoing a cholecystectomy may be as high as 19%. Many of these complications arise from the need for general anesthesia and abdominal insufflation during laparoscopic cholecystectomy procedures. Physiologic changes that patients undergo during general anesthesia and abdominal insufflation may not be tolerated in elderly patients with multiple medical comorbidities. In addition, patients with a history of prior surgery may have intra-abdominal adhesions, making visualization of the gallbladder and surrounding structures more difficult during laparoscopy.

There is a need in the art for an improved methods and devices for use in treating patients with gallbladder disease.

BRIEF SUMMARY OF THE INVENTION

Discussed herein are various cryoablation devices for ablating a gallbladder.

In Example 1, a cryoablation device comprises an elongate body, an expandable balloon operably coupled to the elongate body, a conduit associated with the elongate body, and at least one first suction opening defined in the elongate body. The expandable balloon is configured to receive an ablation fluid, wherein the expandable balloon is further configured to be positionable within a gallbladder. The conduit is operably coupled to the expandable balloon such that the ablation fluid is transportable to the expandable balloon via the conduit.

Example 2 relates to the cryoablation device according to Example 1, wherein the elongate body is a cryoprobe body or a catheter body.

Example 3 relates to the cryoablation device according to Example 1, wherein the at least one first suction opening is defined in the elongate body distal to the expandable balloon.

Example 4 relates to the cryoablation device according to Example 1, wherein the at least one first suction opening is defined in the elongate body proximal to the expandable balloon.

Example 5 relates to the cryoablation device according to Example 1, further comprising at least one second suction opening defined in the elongate body, wherein the at least one first suction opening is defined in the elongate body distal to the expandable balloon and the at least one second suction opening is defined in the elongate body proximal to the expandable balloon.

Example 6 relates to the cryoablation device according to Example 1, wherein the ablation fluid is a cryogen.

Example 7 relates to the cryoablation device according to Example 6, wherein the cryogen is liquid cryogen or gas cryogen.

Example 8 relates to the cryoablation device according to Example 1, further comprising a cryogen lumen defined within the elongate body, wherein the cryogen lumen is configured to receive a cryogen, wherein the ablation fluid is a conductive fluid.

Example 9 relates to the cryoablation device according to Example 1, wherein the elongate body comprises a suction lumen defined therein, wherein the suction lumen is in fluidic communication with the at least one first suction opening.

Example 10 relates to the cryoablation device according to Example 1, wherein the conduit comprises a lumen defined within the elongate body, wherein the lumen is in fluidic communication with an interior of the expandable balloon.

Example 11 relates to the cryoablation device according to Example 1, wherein the expandable balloon comprises at least two lobes, wherein the two lobes are disposed radially adjacent to each other along a length of the elongate body, wherein the at least two lobes define gaps disposed therebetween.

Example 12 relates to the cryoablation device according to Example 11, wherein the at least one first suction opening comprises a plurality of at least one first suction openings defined along the length of the elongate body and within the gaps.

Example 13 relates to the cryoablation device according to Example 1, wherein the elongate body comprises a guidewire lumen defined within the elongate body.

Example 14 relates to the cryoablation device according to Example 1, wherein the expandable balloon comprises at least two lobes, wherein the two lobes are disposed axially adjacent to each other along a length of the elongate body.

In Example 15, a method of performing a gallbladder ablation comprises positioning a cryoablation device within a gallbladder, filling the expandable balloon with cryogen via the cryogen conduit, and causing the gallbladder to contract and thereby contact the expandable balloon by applying suction via a lumen within the elongate body and the at least one first suction opening. The cryoablation device comprises an elongate body, an expandable balloon operably coupled to the elongate body, a cryogen conduit associated with the elongate body, wherein the cryogen conduit is operably coupled to the expandable balloon, and at least one first suction opening defined in the elongate body.\

Example 16 relates to the method according to Example 15, wherein the elongate body is a cryoprobe body or a catheter body.

Example 17 relates to the method according to Example 15, wherein the positioning the cryoablation device within the gallbladder further comprises advancing a guidewire into the gallbladder, and advancing the cryoablation device into the gallbladder over the guidewire.

Example 18 relates to the method according to Example 15, further comprising removing the cryogen from the expandable balloon, thereby causing the expandable balloon to contract, and retracting the cryoablation device from the gallbladder.

In Example 19, a cryoablation device comprises a cryogen probe comprising an elongate probe body, an elongate slidable body, at least one suction opening defined in an outer wall of the elongate slidable body, wherein the at least one suction opening is in fluid communication with the suction lumen, and a fluid tube coupled with the elongate slidable body, the fluid tube comprising a fluid tube lumen in fluid communication with the suction lumen of the elongate slidable body. The elongate slidable body comprises a probe lumen defined within the elongate slidable body, wherein the elongate slidable body is slidably positioned over the elongate probe body such that the elongate probe body is disposed within the probe lumen, and a suction lumen defined within the elongate slidable body.

Example 20 relates to the cryoablation device according to Example 19, wherein the at least one suction opening comprises a plurality of suction openings defined in the outer wall of the elongate slidable body.

Example 21 relates to the cryoablation device according to Example 19, wherein the elongate slidable body is an elongate sleeve.

Example 22 relates to the cryoablation device according to Example 19, further comprising a deployable retention structure disposed along a length of the elongate slidable body.

Example 23 relates to the cryoablation device according to Example 22, wherein the deployable retention structure comprises a deployed configuration and an undeployed configuration.

Example 24 relates to the cryoablation device according to Example 22, wherein the deployable retention structure comprises at least two hinged sections hingedly coupled to the outer wall of the elongate slidable body, wherein the at least two hinged sections are moveable between a deployed configuration and an undeployed configuration.

Example 25 relates to the cryoablation device according to Example 19, wherein the elongate slidable body comprises a substantially flexible material.

In Example 26, a method of performing a gallbladder ablation comprises positioning a cryoablation device within a gallbladder, filling the cryogen probe with cryogen via a cryogen conduit, and causing the gallbladder to contract and thereby contact the elongate slidable body by applying suction via the fluid tube, the suction lumen, and the at least one suction opening. The cryoablation device comprises a cryogen probe comprising an elongate probe body, an elongate slidable body slidably positioned over the elongate probe body, at least one suction opening defined in an outer wall of the elongate slidable body, wherein the at least one suction opening is in fluid communication with the suction lumen, and a fluid tube coupled with the elongate slidable body, the fluid tube comprising a fluid tube lumen in fluid communication with the suction lumen of the elongate slidable body. The elongate slidable body comprises a probe lumen defined within the elongate slidable body, wherein the elongate slidable body is slidably positioned over the elongate probe body such that the elongate probe body is disposed within the probe lumen, and a suction lumen defined within the elongate slidable body.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed or contemplated herein relate to cryoablation device embodiments and related methods for use in minimally invasive gallbladder ablation procedures. The various embodiments utilize a combination of cryoablation and/or suction to maximize the contact between the cryogen and the gallbladder wall while minimizing the size of the cryoablation zone, thereby reducing the risks of damage to other tissues during the procedure. The implementations herein allow for a minimally invasive gallbladder therapy that can be performed under moderate sedation, instead of general anesthesia.

Figure 1A:
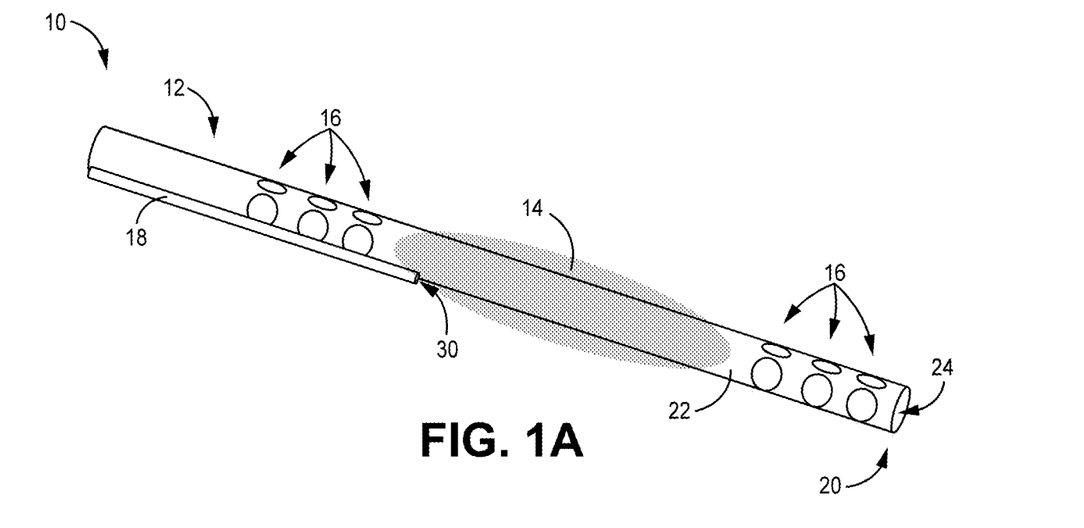
FIG. 1A is a perspective view of a cryoablation catheter, according to one embodiment.
Figure 1B:
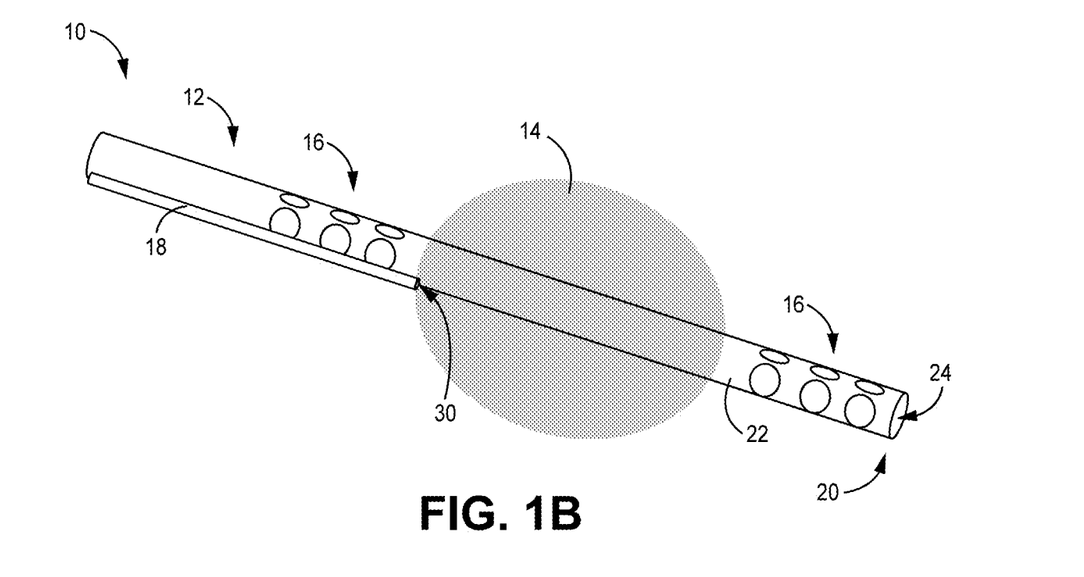
FIG. 1B is a perspective view of the cryoablation catheter of FIG. 1A with the balloon filled with cryogen.

FIGS. 1A and 1B depict a cryoablation device 10, according to one embodiment. This device 10 is a catheter 10 that has a catheter body 12 (which in this specific example is an elongate tube 12), a cryoablation balloon 14, suction openings 16, and a cryogen conduit 18.

In one implementation, the catheter body 12 is made of thermoplastic elastomers (TPE), such as polyether block amide (PEBA), or other polymers. Alternatively, the catheter tube 12 can be made of any known material for a catheter used in interventional radiology. It is understood that any catheter body in any implementation disclosed or contemplated herein can be made of the same or similar materials.

The cryoablation balloon 14 is coupled to, positioned on, or otherwise associated with the body 12 such that the balloon 14 can have both an uninflated state and an inflated or filled state in which the balloon 14 is filled with a cryogen. More specifically, FIG. 1A depicts the balloon 14 in its uninflated state, while FIG. 1B shows the balloon 14 in its filled state. In the specific implementation of FIGS. 1A and 1B, the balloon 14 is spaced from the distal end 20 of the body 12 such that there are suction openings 16 defined in the length of the body 12 between the balloon 14 and the distal end 20. Alternatively, the balloon 14 can be positioned adjacent to the distal end 20 of the body 12. In a further alternative, the balloon 14 can be positioned anywhere along the length of the catheter body 12. The balloon 14 can be made of polyurethane, polypropylene, polyimide, or any other known biocompatible plastics that can be used in such devices. Alternatively, the balloon 14 can be made of any known flexible or elastic material that can be used in medical device balloons for insertion into a patient and can function in the cold temperatures of a cryogen. It is understood that any balloon in any implementation disclosed or contemplated herein can be made of the same or similar materials.

In accordance with one implementation, the cryogen is a gas cryogen or liquid cryogen. For example, in one specific embodiment, the cryogen is nitrogen, helium, neon, or argon. Alternatively, the cryogen can be any known gas or liquid cryogen for use in medical procedures. It is understood that any device according to any implementation disclosed or contemplated herein can use the same or a similar cryogen.

In one embodiment, the balloon 14 is configured to expand to a size of about 50×30×30 mm. Alternatively, the expanded or filled balloon 14 can have a diameter that ranges from about 10 mm to about 70 mm.

The suction openings 16 are defined in the tubular wall 22 of the catheter body 12 such that the openings 16 create fluidic communication between the lumen 24 of the catheter body 12 and the exterior area immediately adjacent to the body 12 and openings 16. In the specific embodiment depicted in FIGS. 1A and 1B, there are openings 16 defined in the body 12 along a length distal to the balloon 14 and along a length proximal to the balloon 14. Alternatively, the openings 16 could be defined along the length of the body 12 solely distally of the balloon 14 or solely proximally of the balloon 14. In this embodiment, it is understood that an external suction source (not shown) is provided that is operably coupled with the device 10 such that it is in fluidic communication with the lumen 24, thereby creating a vacuum in the lumen 24 that causes suction at the openings 16. It is understood that any known device for creating a vacuum in a medical device can be used. It is further understood that any such vacuum source can be used with any of the various embodiments disclosed or contemplated herein that include suction.

The cryogen conduit 18, according to one embodiment as shown, is coupled to the tubular wall 22 of the catheter body 12 and extends from a proximal end (not shown) to the balloon 14. The distal end of the conduit 18 is coupled to the balloon 14 such that the inner lumen 30 of the conduit 18 is in fluid communication with the interior of the balloon 14. In the implementation depicted in FIGS. 1A and 1B, the conduit 18 is coupled to an exterior portion of the tubular wall 22. Alternatively, the conduit 18 is positioned within the lumen 24 of the catheter body 12. The conduit 18 is used to transport cryogen from an exterior cryogen source (not shown) distally into the balloon 14. FIG. 1B depicts the balloon 14 filled with cryogen that was transported via the conduit 18.

In accordance with an alternative implementation, instead of inflating or filling the balloon 14 with cryogen, the catheter body 12 (or a portion thereof) is filled with cryogen and the balloon 14 is filled with a conductive fluid such that the cryogen in the catheter body 12 causes the conductive fluid in the balloon 14 to cool to a temperature that is sufficient for the balloon 14 to cryoablate the gallbladder according to any of the methods described or contemplated herein. In such an embodiment, the conduit 18 would be used to fill the balloon 14 with the conductive fluid, and the catheter body 12 would have at least two lumens (not shown), a first lumen in fluid communication with the openings 16 and configured to apply suction thereto, and a second lumen that can be filled with cryogen.

Figure 2:
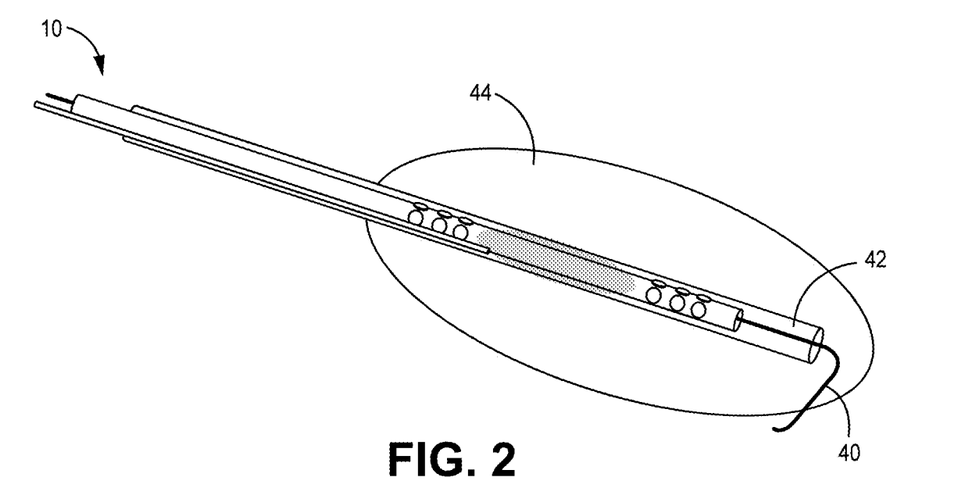
FIG. 2 is a schematic view of the cryoablation catheter of FIG. 1A being inserted into a gallbladder, according to one embodiment.
Figure 3:
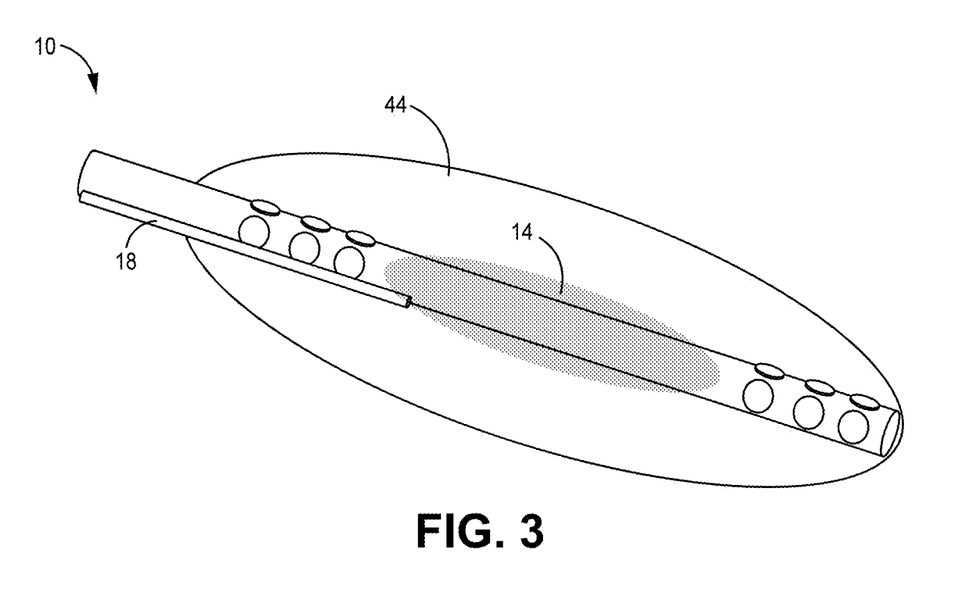
FIG. 3 is a schematic view of the cryoablation catheter of FIG. 1A positioned within a gallbladder, according to one embodiment.
Figure 4:
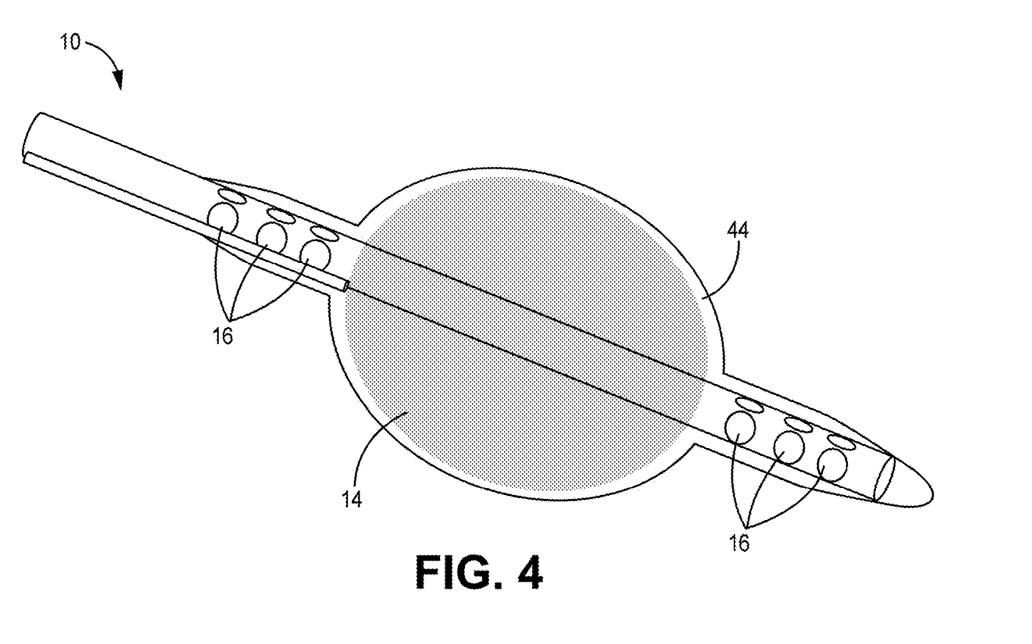
FIG. 4 is a schematic view of the cryoablation catheter of FIG. 1A positioned within a gallbladder with the balloon filled with cryogen and suction applied via the suction openings, according to one embodiment.

In use as best shown with reference to FIGS. 2-4, the cryoablation catheter 10 can be inserted into the gallbladder and perform the ablation using the following steps.

According to one embodiment, a guidewire 40 is first inserted into the gallbladder 44. More specifically, a needle is first used to puncture a hole in the gallbladder 44, and then the guidewire 40 is inserted through the needle and into the gallbladder as desired. The needle is then removed (with the guidewire 40 still in place) and the catheter 10 is then advanced over the guidewire 40 and positioned in the gallbladder 44. In one embodiment as shown in FIG. 2, the catheter 10 is positioned in a sheath 42 before being advanced into the patient over the guidewire 40 and into the gallbladder 44. Alternatively, the sheath 42 can first be advanced over the guidewire 40 and positioned within the gallbladder 44 and then the catheter 10 can subsequently be advanced over the guidewire 40 and into the sheath 42. Once the catheter 10 is positioned as desired, the sheath 42 is removed, as best shown in FIG. 3. Alternatively, a sheath 42 is not used. In one embodiment, the guidewire is a standard 0.035 inch guidewire. Alternatively, any known guidewire for catheter devices can be used. In a further alternative, the device 10 can be inserted without a guidewire.

As shown in FIG. 4, once the catheter 10 is positioned as desired, the balloon 14 is filled with gas or liquid cryogen such that the balloon 14 expands, and suction is applied to the inside of the gallbladder 44 via the catheter lumen 24 and the suction openings 16. The suction reduces the pressure within the gallbladder 44 (in comparison to the pressure outside the gallbladder 44) such that the gallbladder contracts and the wall of the gallbladder adheres to the balloon 14. In one embodiment, the balloon 14 is filled with cryogen before the suction is applied via the suction openings 16. The combination of the expanded balloon 14 filled with cryogen and the contraction of the gallbladder 44 and adherence to the balloon 14 (as a result of the suction) optimizes the effect of the cryogen on the gallbladder 44. That is, the balloon 14 expansion ensures that a substantial cryogenic zone is created while the application of suction maximizes the amount of gallbladder 44 wall that makes contact with the balloon 14, thereby optimizing the effectiveness of the device for purposes of the ablation.

Alternatively, in the implementations in which the cryogen is disposed in the catheter body 12 and a conductive fluid is used to fill the balloon 14, once the catheter 10 is positioned as desired, a cryogen lumen (not shown) in the catheter body 12 is filled with gas or liquid cryogen and the balloon 14 is filled with a conductive fluid such that the balloon 14 expands, and suction is applied to the inside of the gallbladder 44 via the suction lumen (not shown) and the suction openings 16. The suction reduces the pressure within the gallbladder 44 (in comparison to the pressure outside the gallbladder 44) such that the gallbladder contracts and the wall of the gallbladder adheres to the balloon 14. In one embodiment, the balloon 14 is filled with the conductive fluid before the suction is applied via the suction openings 16. The combination of the lumen of the catheter body 12 filled with cryogen, the expanded balloon 14 filled with conductive fluid, and the contraction of the gallbladder 44 and adherence to the balloon 14 (as a result of the suction) optimizes the effect of the conductive fluid on the gallbladder 44.

Figure 5:
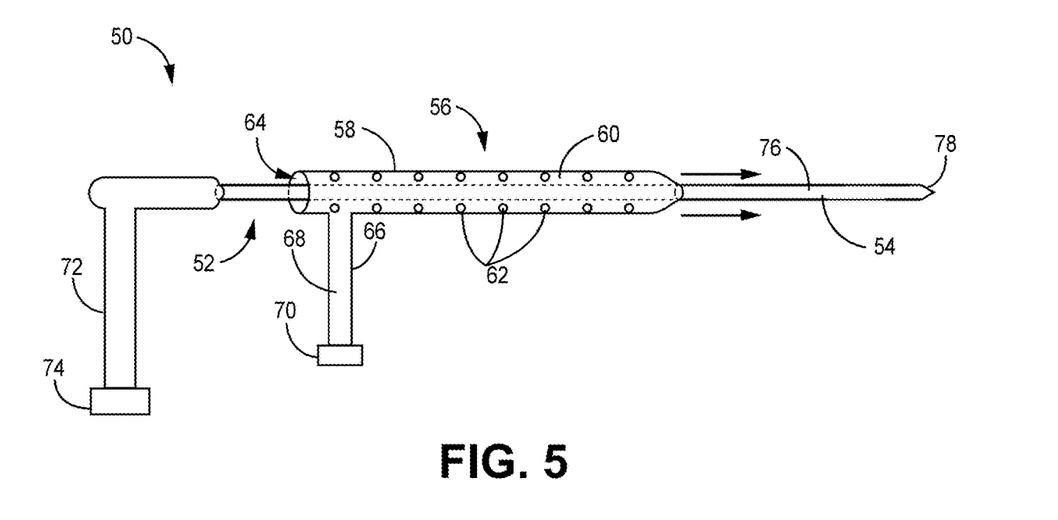
FIG. 5 is a perspective view of a cryoablation device, according to another embodiment.

FIG. 5 depicts another implementation of a cryoablation device 50. This particular device 50 has a cryoablation probe 52 with an elongate probe body 54 and a slidable suction catheter (also referred to herein as a "sleeve") 56 that is positionable over the probe body 54 such that the sleeve 56 is slidable along the length of the body 54. The slidable suction sleeve 56 has a catheter or sleeve body 58 with a tubular wall 60 having suction openings 62 defined therein and an inner lumen 64. Further, the suction sleeve 56 has a fluid tube 66 coupled to the catheter body 58. The fluid tube 66 has a lumen 68 defined therein that is in fluid communication with the inner lumen 64 of the sleeve body 58 and has a tube port (or "suction port") 70 at its proximal end. The probe 52 has cryogen tube 72 extending from a proximal end of the probe body 54, wherein the tube 72 has a cryogen port 74 at the proximal end of the tube 72. Further, the probe body 54 has an inner lumen 76 configured to receive cryogen.

The slidable suction sleeve 56 is slidably positioned over the probe body 54 such that the sleeve 56 can be moved distally or proximally along the body 54. The suction openings 62 defined in the tubular wall 60 of the sleeve 56 create fluidic communication between the inner lumen 64 of the sleeve 56 and the exterior area immediately adjacent to the sleeve 56 and openings 62 such that any vacuum or lowering of air pressure within the inner lumen 64 can cause suction at the suction openings 62 similar to that discussed with respect to the prior embodiment. According to one implementation, there are openings 62 all along the length of the catheter body 58. Alternatively, the openings 62 could be defined along only a distal portion of the catheter body 58 or only along a proximal portion of the body 58. It is understood that the openings 62 can be defined anywhere along the length of the catheter body 58.

In one embodiment, the vacuum or lower air pressure within the inner lumen 64 is caused by suction applied by a suction device (not shown) coupled to the suction port 70 on the fluid tube 66, which decreases air pressure within the fluid tube 66, which thereby decreases air pressure in the inner lumen 64, thereby causing a suction action at the suction openings 62.

In one implementation, the sleeve body 58 is made of polyvinylchloride, nylon, or polyurethane. Alternatively, the catheter body 58 is made of any known polymer, or combination of polymers, that can be used in a medical device catheter body. In a further alternative, the catheter body 58 can be made of any known material for a catheter used in interventional radiology.

The probe 52, in accordance with one embodiment, is a known, conventional cryoprobe. For example, in one embodiment, the cryoprobe can be the R3.8 cryoprobe, which is commercially available from Endocare, Inc., which is part of Healthtronics, Inc. of Austin, Tex. Alternatively, the probe 52 can be a customized cryoprobe. In various embodiments, a cryogen source is coupled to the cryogen port 74 and thereby supplies cryogen to the inner lumen 76 of the probe body 54.

In use, the cryoablation device 50 can be inserted into the gallbladder and perform the ablation using the following steps.

According to one embodiment, the probe body 54 is first inserted into the gallbladder in a fashion similar to the insertion of a guidewire. More specifically, the probe body 54 can have, according to certain embodiments, a sharp distal end 78 of the body 54 that can be used to puncture a hole in the gallbladder, and then the probe body 54 is inserted through the hole and into the gallbladder as desired. At this point, the sleeve 56 has previously been positioned over the probe body 54 or is now positioned over the probe body 54. Regardless, the sleeve 56 is now advanced distally over the probe body 54 and positioned in the gallbladder. Alternatively, the probe body 54 can be configured to be positionable over a guidewire such that a guidewire (not shown) is first inserted into the gallbladder and then the probe body 54 is subsequently advanced into position in the gallbladder over the guidewire. In a further alternative, the sleeve 56 can be inserted over a guidewire (prior to the probe 52). According to one embodiment, a tapered inner dilator can be used to facilitate smooth insertion. Once the sleeve 56 is inserted as desired, the dilator can be retracted (if such a dilator is used) and the probe 52 is inserted into and through the sleeve 56 such that the probe 52 and sleeve 56 are disposed within the gallbladder as desired.

Once the probe body 54 and sleeve 56 are positioned as desired, the probe body 54 is filled with gas or liquid cryogen, thereby significantly lowering the temperature of the probe body 54. In addition, suction is applied to the inside of the gallbladder via the catheter inner lumen 64 and the suction openings 62. The suction can be applied before, at the same time as, or after the provision of the cryogen. As discussed above with the previous embodiment, the suction reduces the pressure within the gallbladder (in comparison to the pressure outside the gallbladder) such that the gallbladder contracts and the wall of the gallbladder adheres to the sleeve 56. The combination of the probe body 54 filled with cryogen and the contraction of the gallbladder and adherence to the sleeve 56 (as a result of the suction) optimizes the effect of the cryogen on the gallbladder. That is, the application of suction maximizes the amount of gallbladder wall that makes contact with the sleeve 56, thereby optimizing the effectiveness of the device for purposes of the ablation.

Figure 6A:
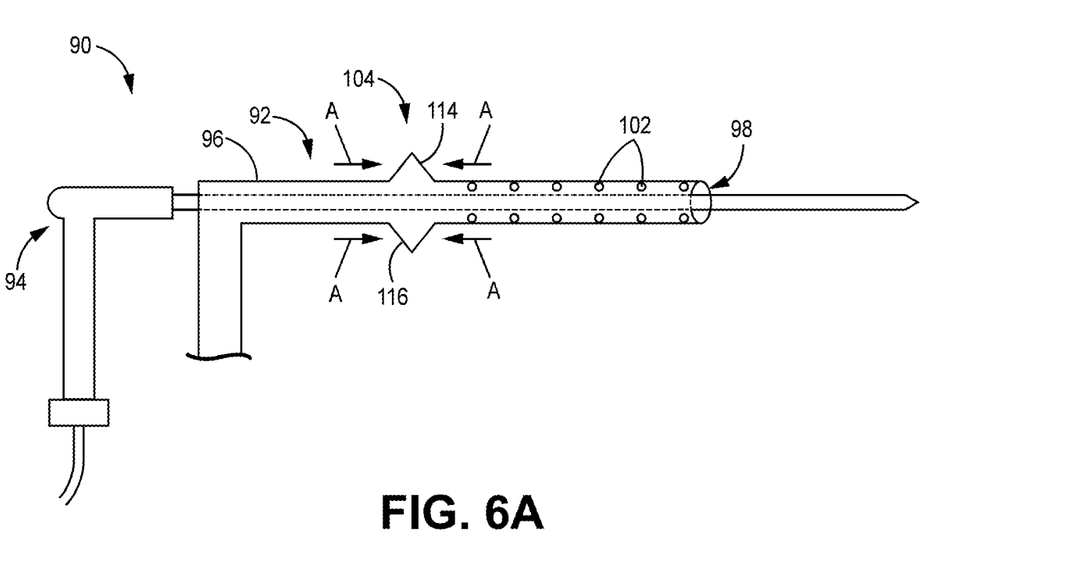
FIG. 6A is a side view of a slidable suction sleeve with a retention mechanism disposed over a cryoprobe, according to one embodiment.
Figure 6B:
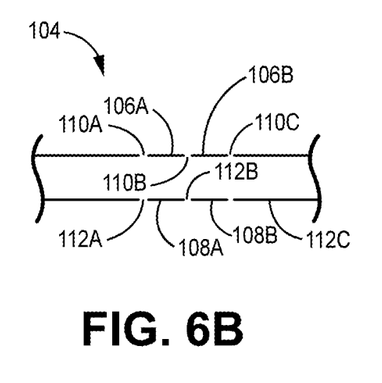
FIG. 6B depicts an expanded view of the retention mechanism of the suction sleeve of FIG. 6A, according to one embodiment.
Figure 6C:
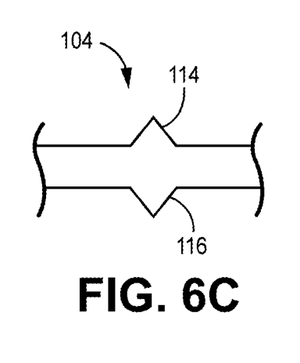
FIG. 6C depicts a further expanded view of the retention mechanism of the suction sleeve of FIG. 6B, according to one embodiment.

FIGS. 6A-6C depict a further embodiment of a system 90 that includes suction sleeve 92 for use with a cryoablation probe 94. It is understood that the cryoablation probe 94 can be substantially the same probe as the probe 52 discussed above with respect to FIG. 5 and thus will not be specifically discussed herein. In this implementation, the slidable suction sleeve 92 is substantially similar to the sleeve 56 discussed above except as to the additional features discussed herein. More specifically, in addition to a sleeve body 96 with an inner lumen 98 and a tubular wall 100 having suction openings 102 and other components and features similar to the sleeve 56 discussed above, the sleeve body 96 in this specific implementation has a deployable retention structure 104 disposed along the length of the sleeve body 96. The retention structure 104 is typically disposed at a location that is closer to the proximal end of the sleeve body 96 than the distal end. Alternatively, the retention structure 104 can be disposed anywhere along the length of the body 96.

In the specific exemplary embodiment depicted in FIGS. 6A-6C, the deployable retention structure 104 is made up of two hinged sections 106A, 106B, 108A, 108B on opposing sides of the sleeve body 96 that are coupled to each other and the sleeve body 96 via joints or hinges 110A, 110B, 110C, 112A, 112B, 112C on each side of each section. As such, the hinged sections can be deployed into two protrusions (also referred to herein as "ridges") 114, 116 that protrude out from the sleeve body 96 as best shown in FIGS. 6A and 6C. More specifically, the hinged sections 106A, 106B, 108A, 108B can be deployed to form the protrusions 114, 116 by urging the distal and proximal ends of the sleeve body 96 toward each other as shown by arrows A in FIG. 6A, thereby causing the hinged sections 106A, 106B, 108A, 108B to begin to rotate in relation to each other at the hinges 110A, 110B, 110C, 112A, 112B, 112C toward the deployed configuration as shown.

Alternatively, the deployable retention structure 104 can be a deployable flange, a deployable disc, an inflatable annular balloon disposed around the sleeve body 96, or any other similar feature or mechanism that can be deployed into a retention structure.

In use, like the cryoablation system 50 discussed above, the probe 94 can be preloaded with the suction sleeve 92. That is, the suction sleeve 92 can be slidably positioned on the probe 94 prior to the procedure. It is understood that the various steps for use of this system 90 are substantially similar to the steps described above with respect to the system 50, except as described herein. More specifically, once the probe 94 and sleeve 92 are positioned as desired in the gallbladder, the deployable retention structure 104 can be deployed as discussed above, thereby helping to retain the sleeve 92 within the gallbladder because the retention structure 104 has a diameter that is greater than the incision or opening in the gallbladder, thereby helping to prevent the sleeve 92 from inadvertently sliding proximally out of the gallbladder. Once the ablation procedure is complete, the retention structure 104 can be urged back into its undeployed configuration prior to retraction of the probe 94 and sleeve 92 from the gallbladder.

Figure 7A:
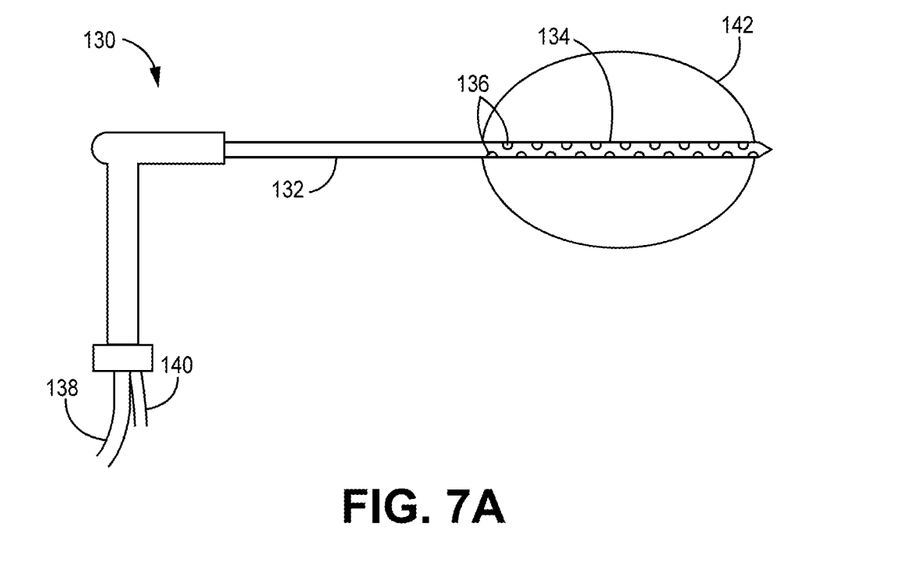
FIG. 7A depicts a side view of a cryoprobe with an expandable balloon, according to one embodiment.
Figure 7B:
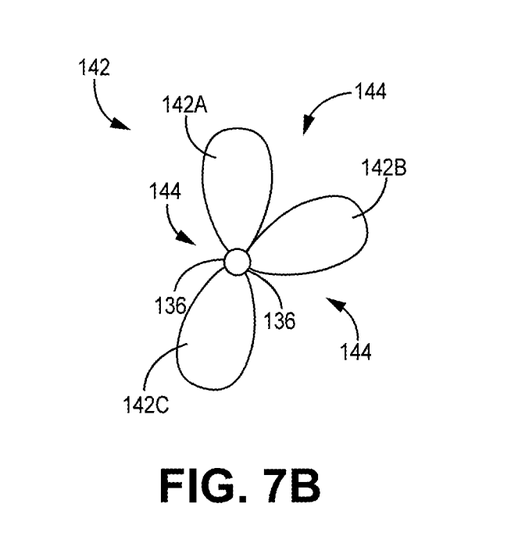
FIG. 7B depicts a cross-sectional front view of the cryoprobe of FIG. 7A, according to one embodiment.

Another embodiment of a cryoablation device 130 is depicted in FIGS. 7A and 7B, which show a cryoablation probe 130. This probe 130 has an elongate probe body 132 with a tubular wall 134 having suction openings 136 defined therein. Further, the probe body 132 has two lumens defined therein: a suction lumen (not shown) in fluid communication with the suction openings 136 and a cryogen lumen disposed along a length of the body 132. The suction lumen (not shown) is also in fluid communication with the suction tube 138 extending from a proximal end of the probe 130, and the cryogen lumen (not shown) is in fluid communication with the cryogen tube 140 which also extends from the proximal end of the probe 130.

The probe 30 also has a cryoablation balloon 142 that is coupled to, positioned on, or otherwise associated with the body 132 such that the balloon 142 can have both an uninflated state and an inflated or filled state in which the balloon 142 is filled with a cryogen, as best shown in FIGS. 7A and 7B. In this specific implementation, the balloon 142 has three lobes 142A, 142B, 142C as best shown in FIG. 7B. Alternatively, the balloon 142 can have two lobes, four lobes, five lobes, or any other number of lobes. In a further alternative, instead of two or more lobes, the balloon 142 is actually made up of two or more balloons. The suction openings 136 are defined in the tubular wall 134 such that they are disposed within the clefts (also referred to as "gaps" or "spaces") 144 between the lobes 142A, 142B, 142C (or balloons) as shown in FIG. 7B. As a result, the suction openings 136 are in fluid communication with the balloon clefts 144 and surrounding area adjacent the clefts 144.

According to one embodiment, the suction openings 136 are disposed along the probe body 132 at or near the distal end of the body 132 and along a length of the body 132 substantially equal to the length of the balloon 142 and adjacent to the balloon 142 such that there are suction openings 136 along the full length of each cleft 144 in the balloon 142. Alternatively, the suction openings 136 can extend beyond the length of the balloon 142. In a further alternative, it is understood that the openings 136 can be defined anywhere along the length of the body 132. In certain alternatives, the balloon 142 can be positioned anywhere along the length of the probe body 132. The balloon 14 can be made of any of the materials described elsewhere herein for any of the balloon embodiments or any other known flexible or elastic material that can be used in medical device balloons for insertion into a patient and can function in the cold temperatures of a cryogen. Further, the cryogen can be any cryogen described with respect to any embodiment herein or any other known gas or liquid cryogen for use in medical procedures.

In this embodiment, it is understood that an external suction source (not shown) is provided that is operably coupled with the device 130 such that it is in fluidic communication with the suction lumen via the suction tube (or "conduit") 138, thereby creating a vacuum in the lumen (not shown) that causes suction at the openings 136. It is understood that any known device for creating a vacuum in a medical device can be used.

The cryogen tube (or "conduit") 140, according to one embodiment as shown, is in fluidic communication with the cryogen lumen (not shown), as discussed, which in turn is in fluidic communication with the interior of the balloon 142. The tube 140 and lumen are used to transport cryogen from an exterior cryogen source (not shown) distally into the balloon 142.

In accordance with an alternative implementation, instead of inflating or filling the balloon 142 with cryogen, the cryogen lumen (not shown) is filled with cryogen and the balloon 142 is filled with a conductive fluid such that the cryogen in the probe body 132 causes the conductive fluid in the balloon 142 to cool to a temperature that is sufficient for the balloon 142 to cryoablate the gallbladder according to any of the methods described or contemplated herein. In such an embodiment, a separate lumen (and tube) (not shown) would be used to fill the balloon 142 with the conductive fluid, and thus the body 132 would have at least three lumens: a cryogen lumen (not shown), a suction lumen (not shown), and a conductive fluid lumen (not shown).

The probe 130, in accordance with one embodiment, is a known, conventional cryoprobe as described elsewhere herein that has been modified as described herein. Alternatively, the probe 130 can be a customized cryoprobe having the features and components described herein.

In use, the cryoablation probe 130 can be inserted into the gallbladder and perform the ablation using steps similar to those described above with respect to the catheter device having a cryoballoon and suction openings. In one embodiment, the probe 130 can be inserted into the gallbladder using a guidewire, or, alternatively, it can be inserted without a guidewire. Once the probe 130 is positioned as desired, the balloon 142 is filled with cryogen and suction is applied via the suction openings 136 in a fashion similar to the methods described elsewhere herein, with the same results and benefits as described therein.

Figure 8:
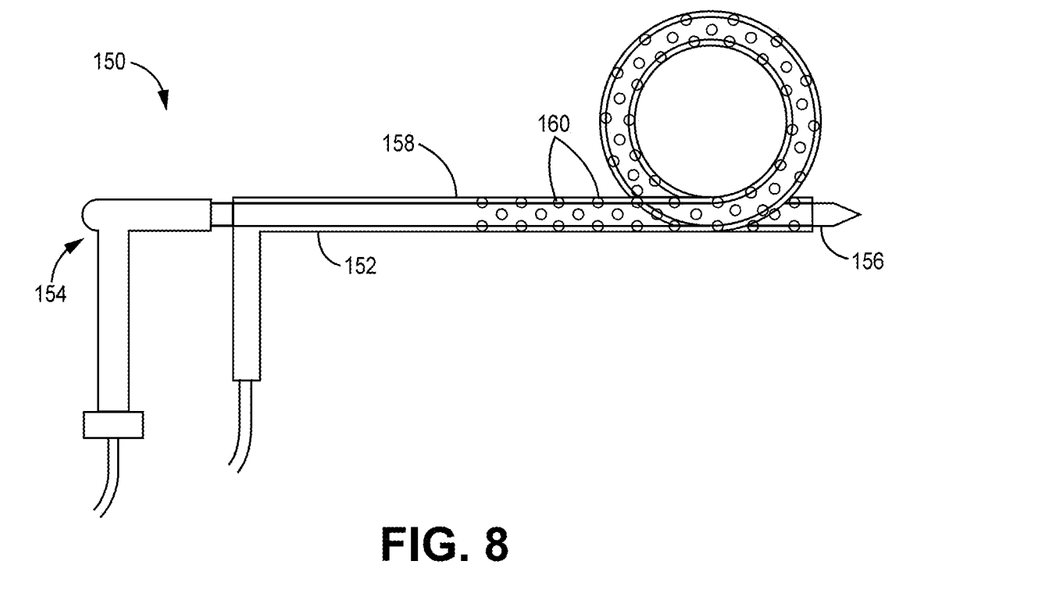
FIG. 8 depicts a side view of a flexible, slidable suction sleeve disposed over a cryoprobe, according to another embodiment.

FIG. 8 depicts a further embodiment of a system 150 that includes a suction sleeve 152 for use with a cryoablation probe 154, which in this case is a flexible, curved cryoablation probe 154. More specifically, the probe 154 in this embodiment is a known probe having a probe body 156 with a flexible, curved configuration. In this implementation, the slidable suction sleeve 152 is substantially similar to the sleeve 56 discussed above except as to the additional features discussed herein. More specifically, the sleeve 152 in this implementation has a flexible sleeve body 158 that is configured to conform to the shape of the probe body 156 in a fashion similar to that shown in FIG. 8 while still having suction openings 160 defined therein in a fashion identical or similar to the system 50 described above.

In use, this system 150 can operate in a fashion similar to the system 50 discussed above. That is, it is understood that the various steps for use of this system 150 are substantially similar to the steps described above with respect to the system 50.

Another embodiment of a cryoablation device 180 is depicted in FIGS. 9A-9D, which show a cryoablation probe 180 having a probe body 182 and an inflatable cryoballoon 184. In accordance with one implementation, the probe body 182 has a cryogen lumen (not shown) defined therein and further has a conductive fluid conduit 186 disposed along a length of the body 182, and more specifically disposed along an outer surface of the body 182. The conductive fluid conduit 186 is in fluidic communication with an interior of the inflatable balloon 184 such that conductive fluid can be transferred along the conduit 186 to fill the balloon 184 as will be described in additional detail below. Alternatively, the conductive fluid conduit 186 can be disposed along an inner surface or other inner portion of the body 182, and thus can, in certain embodiments, constitute a conductive fluid lumen 186. The cryogen lumen (not shown) is substantially similar to the cryogen lumen in any known cryoprobe and allows for circulation of cryogen within the lumen to allow for the cryoprobe to perform an ablation.

The probe body 182 can also have a guidewire lumen (not shown) therein, such that the body 182 can be advanced over a guidewire in certain implementations. In one implementation, the body 182 is made of one or more metals, ceramics, plastics, or other known materials. Alternatively, the probe body 182 can be made of any known material for a probe used in interventional ablation. According to one embodiment, the distal tip of the body 182 is sharp. Alternatively, the tip is blunt. Further, the body 182 can be substantially rigid, or alternatively can be fairly flexible or compliant. It is understood that any probe body in any implementation disclosed or contemplated herein can be made of the same or similar materials and/or have the same or similar features or components.

Figure 9A:
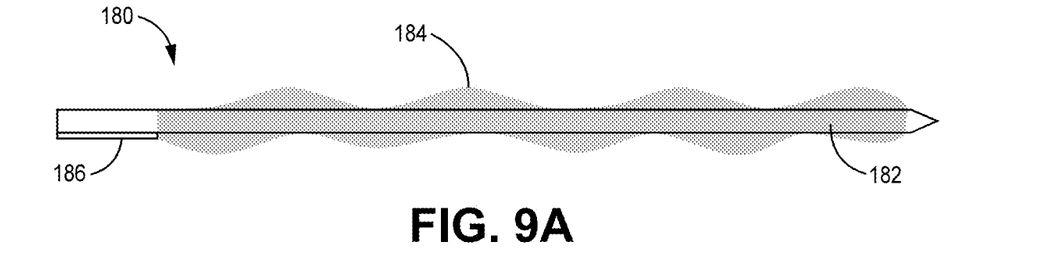
FIG. 9A depicts a side view of a cryoprobe with an expandable balloon in its uninflated state, according to a further embodiment.
Figure 9B:
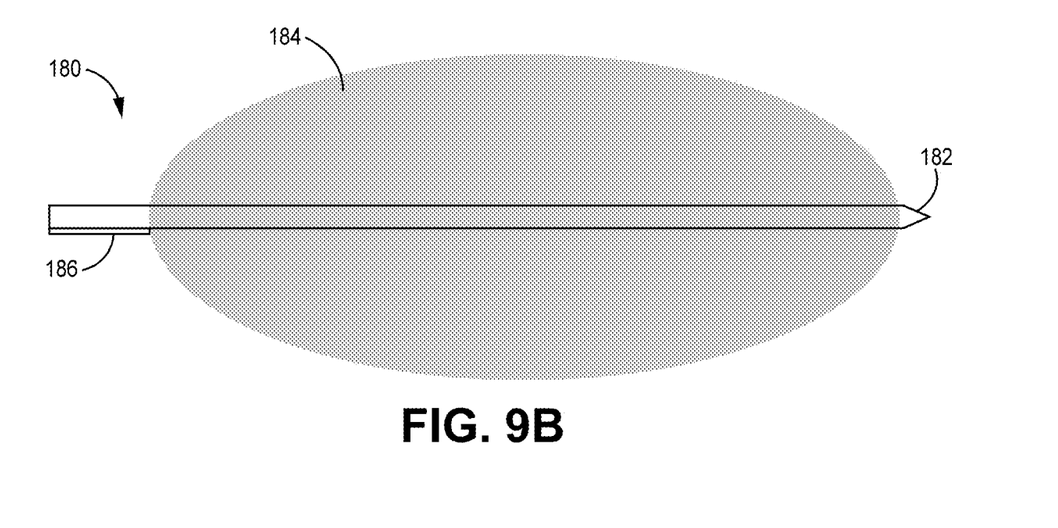
FIG. 9B depicts a side view of the cryoprobe with the expandable balloon of FIG. 9A in its inflated state, according to one embodiment.

The cryoablation balloon 184 is coupled to, positioned on, or otherwise associated with the body 182 such that the balloon 142 can have both an uninflated state (as best shown in FIG. 9A) and an inflated or filled state in which the balloon 142 is filled with the conductive fluid (as best shown in FIG. 9B). The balloon 184 can be made of polyurethane, polyethylene, nylon, latex, PVC, polypropylene, polyimide, or any other known biocompatible polymers or plastics that can be used in such devices. Alternatively, the balloon 184 can be made of any known flexible or elastic material that can be used in medical device balloons for insertion into a patient and can function in the cold temperatures of a cryogen. It is understood that any balloon in any implementation disclosed or contemplated herein can be made of the same or similar materials.

The conductive fluid that can fill the balloon 184 can be biocompatible, have a low freezing point, and have the ability to transmit cold temperatures. In certain implementations, the fluid can be mono-propylene glycol, mono-ethylene glycol, glycerol, and linseed oil. Alternatively, any known conductive fluid for use in a cryoablation device can be used. It is understood that the conductive fluid in any other embodiment disclosed or contemplated herein can be made of the same or similar materials and/or have the same or similar features.

According to one alternative embodiment, the device 180 can have suction openings (not shown) and provide suction in the same fashion as any of the other embodiments herein.

The probe 180, in accordance with one embodiment, is a known, conventional cryoprobe as described elsewhere herein that has been modified as described herein. Alternatively, the probe 180 can be a customized cryoprobe having the features and components described herein.

Figure 9C:
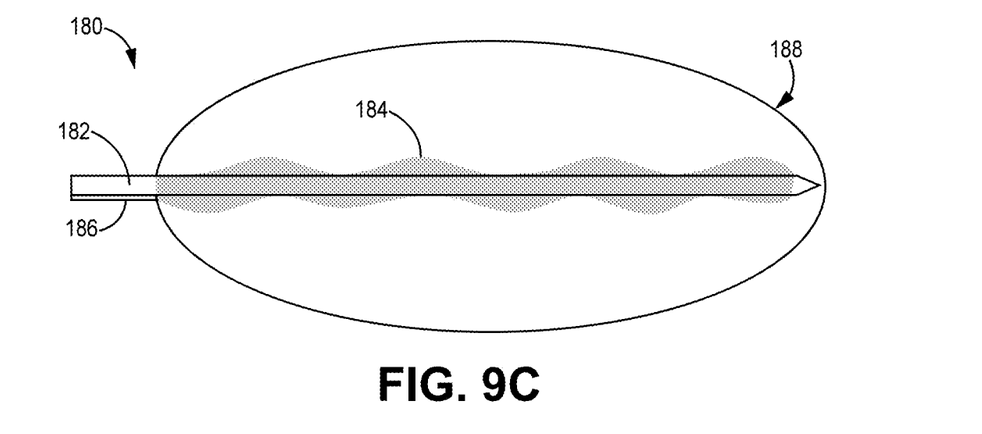
FIG. 9C depicts a side view of the cryoprobe with the expandable balloon of FIG. 9A in its uninflated state after the cryoprobe has been advanced into a patient's gallbladder, according to one embodiment.
Figure 9D:
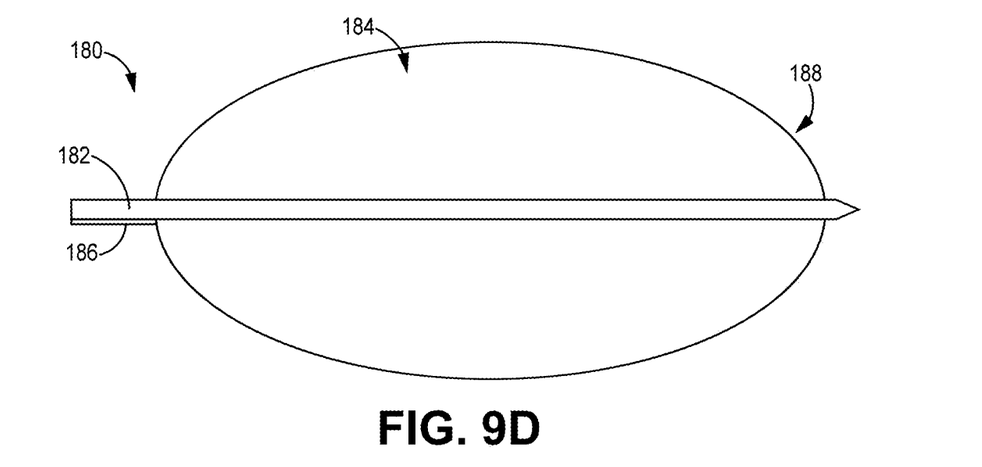
FIG. 9D depicts a side view of the cryoprobe with the expandable balloon of FIG. 9A in its inflated state after the cryoprobe has been advanced into the patient's gallbladder, according to one embodiment.

In use, as best shown in FIG. 9C, the cryoablation probe 180 can first be inserted into the gallbladder 188 with the balloon 184 in its uninflated state. Once the probe 180 is positioned as desired (with the balloon 184 fully within the gallbladder), the balloon 184 can be inflated by providing conductive fluid via the conduit 186, as best shown in FIG. 9D. At the same time (or before or after filling the balloon 184), the cryogen is supplied to the cryogen lumen (not shown) in the cryoprobe body 182, thereby beginning the process of freezing the probe body 182 and thereby causing the temperature of the conductive fluid to lower to the point that the balloon 184 can ablate the gallbladder.

Figure 10A:
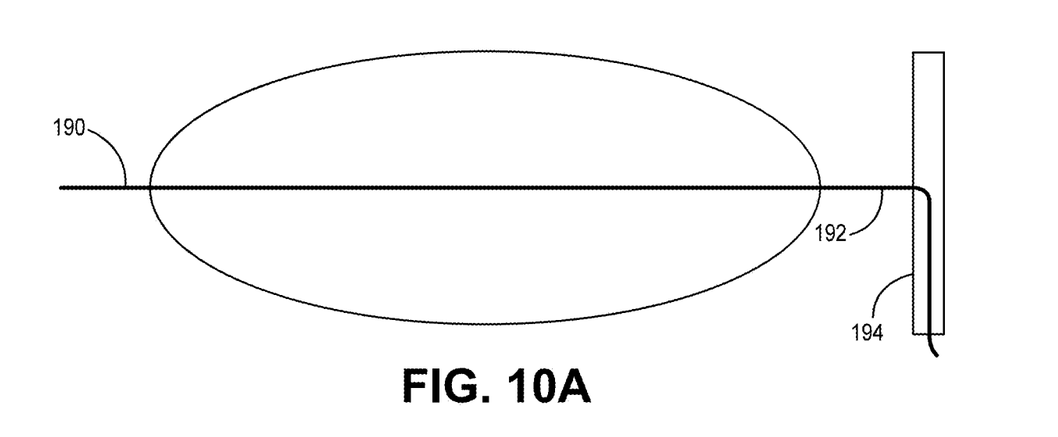
FIG. 10A depicts a side view of a method of using a cryoprobe in which a guidewire is first inserted through the gallbladder, according to one embodiment.
Figure 10B:
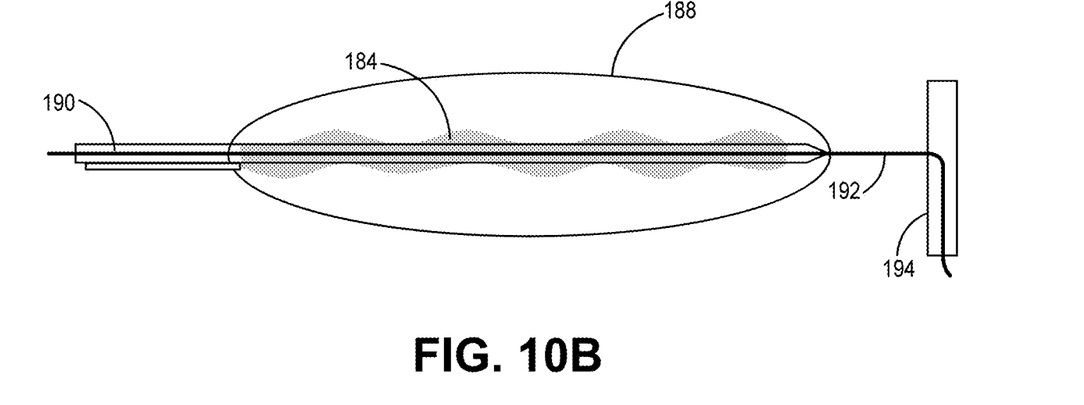
FIG. 10B depicts a side view of the method of using a cryoprobe as depicted in FIG. 10A in which the cryoprobe with an uninflated balloon has been advanced over the guidewire into the gallbladder, according to one embodiment.
Figure 10C:
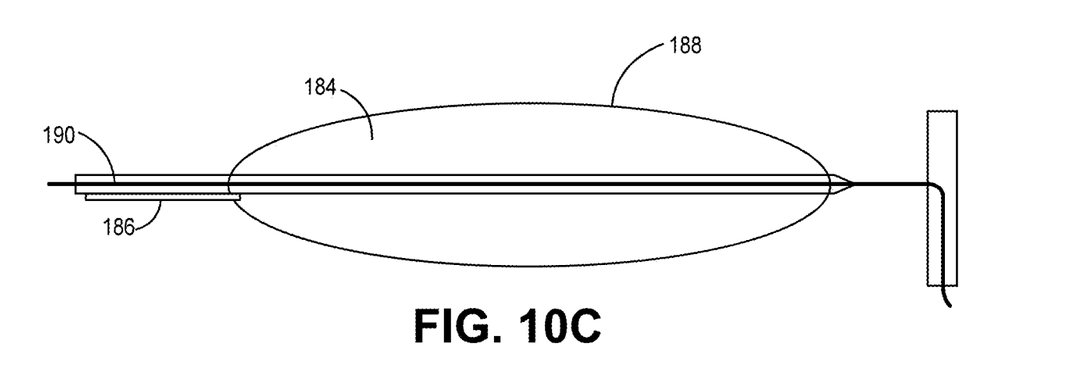
FIG. 10C depicts a side view of the method of using a cryoprobe as depicted in FIG. 10A in which the balloon has been inflated in the gallbladder, according to one embodiment.

Alternatively, the probe 180 can be used in a similar procedure to that described above, except that it is first inserted over a guidewire. That is, as best shown in FIG. 10A, a guidewire 190 is first inserted percutaneously through the gallbladder. Further, in one embodiment, the guidewire 190 is manipulated or steered along the cystic duct 192 and the bile duct 194 as shown. The probe 180 is than advanced over the guidewire 190, with the guidewire being disposed within the guidewire lumen (not shown) in the probe such that the probe 180 can advance over it. The probe 180 is advanced until it is disposed as desired in the gallbladder 188 with the balloon 184 in its uninflated state, as best shown in FIG. 10B. The balloon 184 is then inflated with the conductive fluid via the conduit 186, as best shown in FIG. 10C. Once the ablation is complete, the balloon 184 can be deflated and the probe 180 and guidewire 190 can be retracted.

Figure 11:
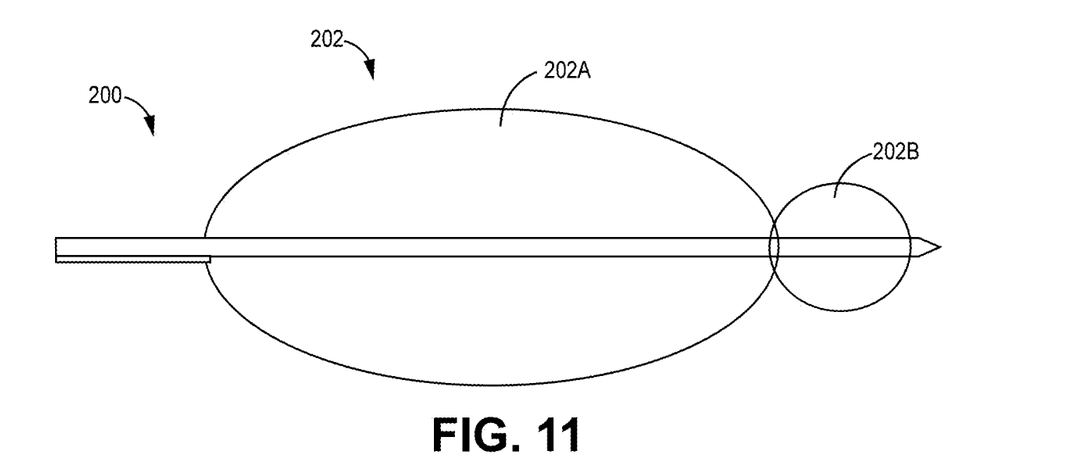
FIG. 11 depicts a side view of a cryoprobe with an expandable balloon that includes two or more lobes (or two or more balloons), according to another embodiment.

In a further alternative embodiment as shown in FIG. 11, the cryoablation probe 200 can have substantially the same components and features as set forth above with respect to probe 180, except as to the specific differences described herein. More specifically, the probe 200 has an inflatable balloon 202 that is made up of at least two lobes 202A, 202B formed by a constraint therebetween or some other similar structure (or, alternatively, to two or more separate balloons 202A, 202B). Alternatively, the number of lobes (or separate balloons) can be three, four, five, six, or more. In this specific example, the distal lobe 202B is smaller than the proximal lobe 202A. According to one embodiment, the specific lobe sizes can be used to design or contour the ablation balloon(s) 202 to better match with the target tissue, thereby resulting in a more focused and controlled ablation. For example, the smaller lobe 202B is sized to match the amount or size of the target tissue at the end of the gallbladder that the distal lobe 202B is intended to contact, thereby reducing the risk of over-ablation or unwanted damage to surrounding tissues. It is understood that the two or more lobes or balloons can be configured in any combination of sizes and configurations to achieve the desired shape and ablation.

Although the present invention has been described with reference to preferred embodiments, persons skilled in the art will recognize that changes may be made in form and detail without departing from the spirit and scope of the invention.

What is claimed is:

1. A method of performing a gallbladder ablation, the method comprising:
    positioning a cryoablation device within a gallbladder, wherein the cryoablation device comprises:
        (a) an elongate body;
        (b) an expandable balloon operably coupled to the elongate body;
        (c) a cryogen conduit associated with the elongate body, wherein the cryogen conduit is operably coupled to the expandable balloon; and
        (d) at least one first suction opening defined in the elongate body;
    filling the expandable balloon with cryogen via the cryogen conduit; and
    causing the gallbladder to contract and thereby contact the expandable balloon by applying suction via a lumen within the elongate body and the at least one first suction opening.

2. The method of claim 1, wherein the elongate body is a cryoprobe body or a catheter body.

3. The method of claim 1, wherein the positioning the cryoablation device within the gallbladder further comprises:
    advancing a guidewire into the gallbladder; and
    advancing the cryoablation device into the gallbladder over the guidewire.

4. The method of claim 1, further comprising:
    removing the cryogen from the expandable balloon, thereby causing the expandable balloon to contract; and
    retracting the cryoablation device from the gallbladder.

5. The method of claim 1, wherein the positioning the cryoablation device within the gallbladder further comprises positioning the cryoablation device within a sheath.

6. The method of claim 1, further comprising positioning the cryoablation device within a sheath.

7. The method of claim 1, wherein the applying the suction can occur before, during, or after the filling the expandable balloon with cryogen.

8. A method of performing a gallbladder ablation, the method comprising:
    positioning a cryoablation device within a gallbladder, wherein the cryoablation device comprises:
        (a) a cryogen probe comprising an elongate probe body;
        (b) an elongate slidable body slidably positioned over the elongate probe body, the elongate slidable body comprising:
            (i) a probe lumen defined within the elongate slidable body, wherein the elongate slidable body is slidably positioned over the elongate probe body such that the elongate probe body is disposed within the probe lumen; and
            (ii) a suction lumen defined within the elongate slidable body;
        (c) at least one suction opening defined in an outer wall of the elongate slidable body, wherein the at least one suction opening is in fluid communication with the suction lumen; and
        (d) a fluid tube coupled with the elongate slidable body, the fluid tube comprising a fluid tube lumen in fluid communication with the suction lumen of the elongate slidable body;
    filling the cryogen probe with cryogen via a cryogen conduit; and
    causing the gallbladder to contract and thereby contact the elongate slidable body by applying suction via the fluid tube, the suction lumen, and the at least one suction opening.

9. The method of claim 8, wherein the positioning the cryoablation device within the gallbladder further comprises:
    advancing a guidewire into the gallbladder; and
    advancing the elongate probe body and the elongate slidable body into the gallbladder over the guidewire, wherein the elongate probe body is advanced over the guidewire before the elongate slidable body or the elongate slidable body is advanced over the guidewire before the elongate probe body or the elongate probe body and the elongate slidable body are advanced over the guidewire together.

10. The method of claim 8, wherein the positioning the cryoablation device within the gallbladder further comprises:
    advancing the elongate slidable body and a dilator into the gallbladder;
    removing the dilator; and
    advancing the elongate probe body into the elongate slidable body in the gallbladder.

11. The method of claim 8, wherein the applying the suction can occur before, during, or after the filling the cryogen probe with cryogen.

12. A method of performing a gallbladder ablation, the method comprising:
    positioning a cryoablation device within a gallbladder, wherein the cryoablation device comprises:
        (a) an elongate body; and
        (b) a cryogenic ablation component associated with the elongate body;
    delivering a cryogen to the cryogenic ablation component; and creating a pressure differential between an interior of the gallbladder and an exterior of the gallbladder such that a wall of the gallbladder contracts around the cryoablation device.

13. The method of claim 12, wherein the creating the pressure differential between the interior of the gallbladder and the exterior of the gallbladder minimizes a cryoablation zone around the cryoablation device and the gallbladder.

14. The method of claim 12, wherein the cryogenic ablation component comprises an expandable balloon or a distal portion of the elongate body.

15. The method of claim 12, wherein the creating the pressure differential comprises applying suction via a suction component associated with the elongate body.

16. The method of claim 12, further comprising positioning the cryoablation device within a sheath.

17. The method of claim 12, further comprising retaining at least a portion of the cryoablation device within the gallbladder by deploying a retention structure associated with the elongate body.

18. The method of claim 12, wherein the elongate body is a cryoprobe body or a catheter body.

19. A method of performing a gallbladder ablation, the method comprising:
 positioning a cryoablation device within a gallbladder, wherein the cryoablation device comprises:
  (a) an elongate body;
  (b) a cryogenic ablation component associated with the elongate body; and
  (c) a suction component associated with the elongate body;
 delivering a cryogen to the cryogenic ablation component; and
 applying suction within the gallbladder via the suction component such that the gallbladder contracts around the cryoablation device.

20. The method of claim 19, wherein the suction component comprises at least one suction opening defined in the elongate body or in an elongate slidable body slidably positioned over the elongate body.

* * * * *